United States Patent [19]

McHughen

[11] Patent Number: 4,616,100

[45] Date of Patent: Oct. 7, 1986

[54] PRODUCTION OF IMPROVED PLANTS HAVING AN INCREASED TOLERANCE TO THE PRESENCE OF A NORMALLY DELETERIOUS CONCENTRATION OF A PLURALITY OF INORGANIC SALTS

[75] Inventor: Alan G. McHughen, Saskatoon, Canada

[73] Assignee: Crop Development Centre of the University of Saskatchewan, Saskatoon, Canada

[21] Appl. No.: 574,052

[22] Filed: Jan. 26, 1984

[51] Int. Cl.[4] .......................... A01B 79/00; C12N 5/00
[52] U.S. Cl. ........................................ 800/1; 435/240; 47/58
[58] Field of Search ................................ 435/240, 241

[56] References Cited

PUBLICATIONS

Nabors et al., 1975, Plant Sci. Lett., vol. 4, pp. 155–159.
Dix et al., 1975, Plant Sci. Lett., vol. 5, pp. 231–237.
Epstein et al., 1980, Science, vol. 210, pp. 399–404.
Nabors et al., 1980, Z. Pflanzenphysiol., vol. 97, 13–17.
Orton, 1980, Z. Pflanzenphysiol., vol. 98, pp. 105–118.
Progress Report—Tissue Culture for Crops, 1982.
Henke, 1981, Envir. and Exp. Bot., vol. 21 (3/4), 347–57.
Kochba et al., 1982, Z. Pflanzenphysiol., vol. 106, pp. 111–118.
Nabors et al., 1982, Z. Pflanzenphysiol., vol. 105, pp. 341–349.
Chaleff, 1983, Science, vol. 219, 676–82.
Evans et al., 1983, Science, vol. 221, 949–51.
Rangan et al., 1983, Ann. Bot., vol. 52, 59–64.
Conger (Editor), 1981, Cloning Agricultural Plants Via In Vitro Techniques, pp. 195, 211, CRC Press, Boca Raton.
Allard, 1960, Principles of Plant Breeding, John Wiley & Sons, N.Y., pp. 38–40, 43–47.

Primary Examiner—Thomas G. Wiseman
Assistant Examiner—Joanne M. Giesser
Attorney, Agent, or Firm—Burns, Doane, Swecker & Mathis

[57] ABSTRACT

A process is defined for providing plants of a nonhalophytic crop wherein the resulting plants have an enhanced ability to grow successfully in a soil comprising a normally deleterious concentration of a plurality of inorganic salts. Tissue culturing of a large quantity of plant cells initially is carried out under conditions wherein substantial disorganized cell growth takes place which is accompanied by genetic variation (e.g., via somaclonal variation), and the resulting cells subsequently are tissue cultured in a medium which is substantially lacking in a hormone component comprising a plurality of inorganic salts which are provided in a concentration which is normally injurious to cells of the crop wherein a substantial quantity of cells are killed and at least one cell survives and multiplies which has undergone genetic variation wherein an atypical functioning single gene is present which is dominant for increased tolerance to the totality of the inorganic salts present. Living cells which possess the desired genetic variation are recovered and are regenerated into improved plants. The highly desirable plant characteristics made possible by the present process readily can be transferred to subsequent generations in a highly stable manner via plant breeding thereby efficiently providing a new source of improved germ plasm. In a particularly preferred embodiment, improved flax plants and seed capable of forming the same are provided.

45 Claims, No Drawings

PRODUCTION OF IMPROVED PLANTS HAVING AN INCREASED TOLERANCE TO THE PRESENCE OF A NORMALLY DELETERIOUS CONCENTRATION OF A PLURALITY OF INORGANIC SALTS

BACKGROUND OF THE INVENTION

It long has been recognized by plant scientists that soils encountered in many parts of the world are considered to be saline in nature since they include a sufficiently high concentration of water-soluble inorganic salts of a substantially neutral pH to impair the normal functioning of many plants.

Representative inorganic salts which when present in excess can interfere with one or more plant functions are sodium sulfate (Glauber's salt), magnesium sulfate (Epsom salt), calcium sulfate (gypsum), sodium chloride, magnesium chloride, calcium chloride, etc. When such salts are present in a concentration level above an observable threshold level, it is found that a non-halophytic plant when grown in the same is impaired, with such impairment becoming more severe as the inorganic salt concentration increases. A plurality of these salts in injurious concentrations commonly are simultaneously encountered at a given location. Such salts often impede one or more of the following: germination, emergence, normal plant growth, and seed set following emergence. Additionally, plants affected by soil salinity often have an undesirable bluish green appearance.

It has been observed that harmful soil salinity can be encountered at locations which are far removed from present day oceans. For instance, soil salinity is frequently a problem in the Great Plains area of the United States and Canada, and in many arid and semi-arid areas where crop irrigation is a common agricultural practice. In some areas a solid crust of salts may be observed on the soil surface where it is deposited as the salts move upward by capillary action and the water evaporates. In other areas streaks of salt may be observed in the soil below the soil surface. Alternatively, the deleterious salt concentration may be dispersed in a non-visible manner as largely dissolved ions throughout the soil.

The salts may have been imparted to the soil by the weathering of rocks or minerals, or during ancient times the salts may have been introduced into the soil by the evaporation of seas or by glacier deposits. Modern agricultural practices such as irrigation may also impart increasing salt concentrations when the available irrigation water evaporates and leaves previously dissolved salts behind unless such salts are somehow flushed into the ground water and away from the plant roots.

It commonly is believed that excessive concentrations of water-soluble inorganic salts in the soil work to deprive non-halophytic plants of the water and nutrients which they need. The dissolved salts in the soil can serve to increase the osmotic pressure of the solution of the same in the soil with this solution being more concentrated than the sap in the plant roots. This accordingly tends to decrease the rate at which water from the soil will enter the roots. If the solution in the soil becomes too saturated with dissolved salts, the water may actually be withdrawn from the plant roots. Thus the plants slowly starve though the supply of water and dissolved nutrients may be more than ample. Also, elements such as sodium are known to be toxic to plants when they are taken up by the plants. For additional information see reports of Saskatchewan Agriculture, Plant Industry Branch, entitled (1) "Understanding Salt-Affected Soils" by H. M. Holm and J. L. Henry, March, 1982, and (2) "Soil Salinity—A Study in Crop Tolerance and Cropping Practices" by H. M. Holm, March, 1983.

The need to develop plants which are resistant to sodium chloride has received considerable recognition by plant scientists in the past. While some plants are known which are considered to be halophytes (i.e. salt growing plants) and to grow reasonably well in the presence of saline soil, these plants often are weed species of little economic importance such as the Russian thistle, kochia, wild barley, goosefoot, samphire, desert salt grass (*Distichlis stricta*), greasewood (*Sorobatus vermiculatus*), etc. Accordingly, readily available salt tolerant crop germ plasm commonly has not been conveniently available to improve important plants, such as flax, etc. Additionally, conventional plant breeding techniques would be expected to be complex and unusually time consuming. Another complicating factor has been the marked tendency of plants to physiologically adapt to the presence of salts to some degree following exposure to the same, but to be unable to transfer such salt tolerance to progency over a number of successive generations. These epigenetic effects can lead to spurious selections which are of no real value.

When plant cells are placed in vitro, it has been recognized that spontaneous chromosomal aberrations may occur as reported in the 1981 review article by M. J. Constantin, "Chromosome Instability in Cell and Tissue Cultures and Regenerated Plants", *Envir. and Exper. Bot.* 21, 359-368 (1981). Presumably these changes can affect any part of a genome and are the basis of somoclonal variation—a genetically stable phenotypic change observable at the level of the whole plant. See also the article by P. J. Larkin and W. R. Scowcroft "Somoclonal Variation—A Novel Source of Variability From Cell Cultures for Plant Improvement", *Theor. Appl. Genet.* 60, 197-214 (1981).

In vitro tissue culture has been pursued in the past as a possible means to develop plants which are more tolerant to sodium chloride or to sea water. Representative articles which discuss this tissue culture approach are as follows:

Nabors, M. W., Daniels, A., Nadolny, L. and Brown, C., 1975. Sodium Chloride Tolerant Lines of Tobacco Cells. *Plant Sci. Lett.* 4; 155-159.

Dix, P. J. and Street, H. E., 1975. Sodium Chloride-Resistant Cultured Cell Lines From *Nicotiana sylvestris* and *Capsicum annuum.*, *Plant Sci. Lett.* 5; 231-237.

Epstein, E., Norlyn, J. D., Russ, D. W., Kingsbury, R. W., Kelley, D. B. Cunningham, G. A. and Wrona, A. F., 1980. Saline Culture of Crops: A Genetic Approach. *Science* 210: 399-404.

Nabors, M. W., Gibbs, S. E., Berstein, C. S. and Meis, M. E., 1980. NaCl-Tolerant Tobacco Plants From Cultured Cells. *Z. Pflanzenphysiol.* 97; 13-17.

Orton, T. J., 1980. Comparison of Salt Tolerance Between *Hordeum vulgare* and *H. jubatum* in Whole Plants and Callus Cultures. *Z. Pflanzenphysiol.* 98; 105-118.

Department of Botany and Plant Pathology, Colorado State University, Fort Collins, Colo., Oct. 1, 1982, Progress Report Tissue Culture for Crops.

Henke, R. R., 1981. Selection of Biochemical Mutants in Plant Cell Cultures: Some Considerations., *Envir. and Exp Bot*, 21, No. 3/4; 347–357.

Kochba, J., Ben-Hayyim, G., Spiegel-Roy, P., Saad, S. and Neumann, H., 1982. Selection of Stable Salt-Tolerant Callus Cell Lines and Embryos in *Citrus sinensis* and *C. aurantium*. *Z. Pflanzenphysiol.* 106; 111–118.

Nabors, M. W., Kroskey, C. S. and McHugh, D. M., 1982. Green Spots Are Predictors of High Callus Growth Rates and Shoot Formation in Normal and Salt Stressed Tissue Cultures of Oats. *Z. Pflanzenphysiol. Bd.* 105; 341–349.

Chaleff, R. S., 1983, Isolation of Agronomically Useful Mutants From Plant Cell Cultures, *Science*, 219; 676–682.

Evans, D. A. and Sharp, W. R., 1983. Single Gene Mutations in Tomato Plants Regenerated From Tissue Culture. *Science* 221; 949–951.

Rangan, T. S. and Vasil, I. K., 1983. Sodium Chloride Tolerant Embryogenic Cell Lines of *Pennisetum americanum* (L.) K. Schum. *Ann. Bot.* 52; 59–64.

It is indicated in the available technical literature that Nabors and co-workers have used tissue culture technology to identify tobacco and oat cells which are tolerant to a single salt (typically NaCl), and have regenerated NaCl tolerant plants from such cultures. Other researchers commonly have failed to report the successful regeneration from their tissue cultures of functioning plants which continue to possess salt tolerance in subsequent generations. Also, the article by Kochba et al points out that tolerance to one salt does not necessarily confer tolerance to other salts. Since saline soils typically contain several different salts in deleterious concentrations, the grower has heretofore received no real aid from tissue culture research to overcome seemingly intractable problems inherent in salt-affected soils. Accordingly, little practical knowledge has been available in the past concerning how to impart meaningful saline tolerance to field grown crops.

It is an object of the present invention to provide plants having an increased tolerance to the presence of a normally deleterious concentration of a plurality of inorganic salts.

It is an object of the present invention to enable growers to successfully grow crops in areas where harmful soil salinity attributable to a plurality of inorganic salts previously made satisfactory yields impossible.

It is an object of the present invention to enable growers of crops to produce enhanced crop yields in saline soils which include a plurality of deleterious inorganic salts.

It is an object of the present invention to provide plants which are capable of both growth and yield in soils containing a normally deleterious concentration of a plurality of water-soluble salts which are comparable to those obtained in a non-saline soil.

It is an object of the present invention to provide an improved tissue culture technique which has been found capable of simultaneously activating a latent genetic mechanism found to be endogenous to a plant which imparts improved tolerance to a plurality of inorganic salts.

It is another object of the present invention to provide an improved process for increasing the tolerance of crops to a plurality of water-soluble inorganic salts which does not require an extensive plant breeding program involving numerous crosses.

It is a further object of the present invention to provide the formation of the first known *Linum usitatissimum* plants and seed capable of forming the same which exhibit substantial tolerance to a normally deleterious concentration of a plurality of water-soluble inorganic salts.

These and other objects, as well as the scope, nature, and utilization of the claimed invention will be apparent to those skilled in the art from the following detailed description and appended claims.

SUMMARY OF THE INVENTION

It has been found that an improved process for providing plants of a non-halophytic angiosperm crop which is capable of undergoing self-pollination having an enhanced ability to grow successfully in a soil comprising a normally deleterious concentration of a plurality of inorganic salts comprises:

(a) tissue culturing in vitro in a first culture medium a substantial quantity of cells derived from at least one of the plants of the non-halophytic angiosperm crop in the absence of a deleterious concentration of inorganic salts wherein substantial disorganized cell growth takes place which is accompanied by genetic variation, (b) tissue culturing in vitro cells from the first culture medium in a second culture medium which is substantially lacking in a hormone component and comprises a plurality of inorganic salts which are provided in a concentration which is normally injurious to cells of the crop wherein a substantial quantity of the cells are killed and at least one cell survives and multiplies which has undergone genetic variation wherein an atypical functioning single gene is present which is dominant for increased tolerance to the totality of salts present in the normally injurious concentration in the second culture medium, (c) recovering from the second culture medium living cells which possess the genetic variation, and (d) regenerating at least one complete plant from the cells which were recovered in step (c).

It additionally has been found that an improved process for providing plants of a non-halophytic angiosperm crop which is capable of undergoing self-pollination having an enhanced ability to grow successfully in a soil comprising a normally deleterious concentration of a plurality of inorganic salts comprises:

(a) tissue culturing in vitro in a first culture medium a substantial quantity of cells derived from at least one of the plants of the non-halophytic angiosperm crop in the absence of a deleterious concentration of inorganic salts wherein substantial disorganized cell growth takes place which is accompanied by genetic variation, (b) tissue culturing in vitro cells from the first culture medium in a second culture medium which is substantially lacking in a hormone component and comprises a plurality of inorganic salts which are provided in a concentration which is normally injurious to cells of the crop wherein a substantial quantity of the cells are killed and at least one cell survives and multiplies which has undergone genetic variation wherein an atypical functioning single gene is present which is heterozygous dominant for increased tolerance to the totality of salts present in the normally injurious concentration in the second culture medium, (c) recovering from the second culture medium living cells which possess the genetic variation, (d) regenerating at least one complete first generation plant from the cells which were recovered in step (c), (e) self-pollinating the at least one functioning first generating plant from step (d) to form seed thereon, (f) growing the seed from step (e) to form second generation plants, (g) selecting those second generation plants from step (f) which exhibit increased tolerance to the totality of salts present in the normally injurious concentration in the second culture medium and allowing seed to form thereon following self-pollination, (h) growing the seed from step (g) to form third generation plants, and (i) selecting those third generation plants which possess a single gene which is homozygous dominant for increased tolerance to the totality of salts present in the normally injurious concentration in the second culture medium.

In a preferred embodiment a *Linum usitatissimum* seed product is provided consisting of a substantially homogeneous assemblage of seeds which upon germination yield flax plants which exhibit an enhanced ability to grow successfully in soil comprising a normally deleterious concentration of a plurality of inorganic salts wherein the enhancement in salt tolerance to the totality of the inorganic salts is attributable to the presence of a single homozygous dominant gene for such characteristic.

In a further preferred embodiment plants of *Linum usitatissimum* are provided which exhibit an enhanced ability to grow successfully in soil comprising a normally deleterious concentration of a plurality of inorganic salts wherein the enhancement in salt tolerance to the totality of the inorganic salts is attributable to the presence of a single homozygous dominant gene for such characteristic.

DESCRIPTION OF PREFERRED EMBODIMENTS

The plant tissue which is selected for use as the starting material in the process of the present invention is obtained from a non-halophytic angiosperm crop which is capable of undergoing self-pollination. The plants of such crop are true flowering plants which normally are harmed if growth is attempted in a saline soil. For each such crop there is an observable threshold concentration level for the presence of water-soluble inorganic salts in the soil beyond which normal plant functions are impaired. Once the threshold level is reached the impairment of one or more normal plant functions increases approximately linearly with increasing concentrations of water-soluble inorganic salts in the soil. Such plants commonly are termed non-halophytic since they are sensitive to excess salinity in the soil which usually leads to reduced crop yields when the electrical conductivity caused by the salts reaches approximately 4 to 12 mS/cm., or more (e.g. reaches an electrical conductivity of approximately 8 mS/cm.) due to the presence of the water-soluble inorganic salts. Such soil conductivity measurement can be made in situ by standard procedures using a soil contacting Wenner Array four probe resistivity meter or other equivalent device. Representative water-soluble inorganic salts commonly encountered in such saline soils are alkali metal salts, alkaline earth metal salts, and mixtures of alkali metal salts and alkaline earth metal salts. These commonly include sodium sulfate, magnesium sulfate, calcium sulfate, sodium chloride, magnesium chloride, calcium chloride, etc.

Angiosperm crops suitable for improvement in accordance with the process of the present invention include grain crops, forage crops, seed propagated fruits, and industrial species. For the purposes of the present invention grain crops are those which are grown primarily for seed, and forage crops are those which are grown primarily for the consumption of plant parts other than seed such as the foliage or other vegetative structure.

Representative grain crops which may be improved in accordance with the process of the present invention include cereals (e.g., wheat, oats, barley, rye, corn, triticale, sorghum, etc.), grain legumes (e.g., field beans, peas, peanuts, lentils, etc.), and oilseeds (e.g. flax, mustard, safflower, sunflowers, soybeans, rape, etc.). Representative forage crops include alfalfa, sugar beets, onions, peppers, seed propagated potatoes, turnips, cabbage, broccoli, bromegrass, sweet clover, wheatgrass, ryegrass, etc. Representative seed propagated fruits include tomatoes, peppers, watermelons, etc. Representative industrial species include cotton, fibre flax, tobacco, etc.

In a preferred embodiment of the process of the invention the non-halophytic angiosperm crop is *Linum usitatissimum* (e.g. oilseed flax). For instance, as reported in "Soil Salinity—A study in Crop Tolerances and Cropping Practices" (identified earlier), if the soil exhibits an electrical conductivity of 8 mS/cm. a common variety of flax commonly can be expected to yield only approximately 40 percent of the amount possible if the soil were of lower salinity.

The plant cells derived from a non-halophytic angiosperm crop which are subjected to tissue culture in accordance with the process of the present invention may be derived from any part of the plant which is amenable to tissue culture in vitro. Representative sources of plant tissue include stems, leaves, shoot tips, root tips, callus, single cells, and pollen grains. In a preferred embodiment the tissue is derived from one or more seedling plants. Particularly good results are obtainable with *Linum usitatissimum* if the tissue is obtained from the hypocotyl or the cotyledon.

A substantial quantity of the plant cells derived from a non-halophytic angiosperm crop are tissue cultured in vitro in a first culture medium wherein substantial disorganized cell growth takes place which is accompanied by genetic variation. Such tissue culturing can be carried out in conventional tissue culture media for the respective crops, and can be carried out either (1) on a support (e.g. on a semi-solid agar support) to form a callus, or (2) in an aqueous suspension. Standard inorganic salts commonly are included in the culture media in a non-deleterious concentration, as are vitamins and nutrients to support cell life, hormones to stimulate rapid in vitro cell growth, and a carbon source (e.g., sucrose).

In order to increase the probability that the desired genetic variation will be manifest on a reliable basis at least 5 million cells derived from the non-halophytic angiosperm crop preferably are initially provided in the first culture medium For instance, at least 10 million cells, or even 100 million, or more, cells initially can be tissue cultured in vitro in the first culture medium.

While present in the first culture medium, rapid cell growth is stimulated so that the cells live and multiply in a disorganized or amorphous manner. Representative hormones which may be employed either alone or in combination are of the auxin class (e.g. 2,4-D, 2,4,5-T, indolebutyric acid, indoleacetic acid), or of the cytokinin class (e.g., kinetin, benzylamino-purine, zeatin), etc. The nature of the hormone selected is not critical to the operation of the process of the present invention as long as a relatively rapid in vitro disorganized cell growth is encouraged wherein genetic variation is free to occur. For instance, conventional tissue media, such as the Murashige and Skoog medium [See *Physiol. Plant.* 15, 473–479 (1962)], Norstog's $B_{11}$ medium [See *In Vitro* 8: 307–308 (1973)], etc. may be employed. The hormone is substantially lacking in the second culture medium as indicated hereafter.

One or more mutagens optionally concomitantly may act upon the cells while present in the first culture medium. Representative mutagenic agents include ethylmethanesulfonate, gamma rays, X-rays, etc. It should be recognized, however, that the use of a mutagen is not required in order to successfully carry out the process of the present invention. In fact, in a preferred embodiment mutagens are omitted and the genetic variation which occurs is believed to be substantially exclusively via somaclonal variation. In such instance the genetic variation which occurs is spontaneous in nature. Regardless of whether a mutagen is present the cells preferably are provided in the first tissue culture medium for at least 30 days, and most preferably for at least 40 days.

In accordance with the concept of the present invention while the cells are cultured in vitro in the first culture medium, it is believed that a latent genetic mechanism is infrequently but reliably activated which is endogenous within the cells and which imparts the desired improved tolerance to the simultaneous presence of a plurality of normally injurious inorganic salts. Such genetic variation, regardless of its actual causal mechanism, yields an atypical functioning single gene which previously was not operational which is dominant for increased tolerance to the simultaneous presence of a plurality of inorganic salts in a normally injurious concentration. In the past it was not known that a single gene could impart increased tolerance to a plurality of water-soluble inorganic salts and that this tolerance could be transferred to subsequent generations on a reliable basis. Such gene may be either heterozygous dominant (i.e., Aa) or homozygous dominant (i.e. AA) for such characteristic. In the vast majority of instances the gene will be heterozygous dominant for such characteristic based upon statistical probabilities instead of being homozygous dominant for such characteristic. However, the heterozygous dominant character can be readily transformed into a more advantageous homozygous dominant character by conventional plant breeding techniques as described hereafter. It further should be recognized that the genetic changes which occur in the first culture medium are not limited to the specific genetic variation required in the present process. However, when the desired genetic change does not occur the unwanted cells so modified will be eliminated in the second culture medium as described hereafter.

The cells which have been tissue cultured in the first culture are next isolated and are transferred to a second culture medium. Callus cells can be removed by excision and mobile cells can be removed from a suspension by the use of a centrifuge. The second culture medium comprises the basal nutrient medium plus a plurality of inorganic salts which are provided in a concentration which is normally injurious (i.e., normally lethal) to the cells wherein a substantial quantity of the cells are killed and at least on cell survives and multiplies which has undergone genetic variation wherein an atypical functioning single gene is present which is dominant (i.e., either heterogenous dominant or homogeneous dominant) for increased tolerance to the totality of the salts present in a normally injurious concentration in the second culture medium. In the second tissue culture medium conventional tissue culture techniques can again be employed with the exception of the required presence of the normally injurious concentration of a plurality of inorganic salts and a hormone component is substantially lacking as indicated hereafter. In a preferred embodiment, the plurality of inorganic salts provided in the second culture medium each correspond qualitatively to the deleterious salts normally encountered in a predetermined growing area where plant growth of the crop normally is impaired and the respective quantities of the plurality of deleterious inorganic salts at least approximate (e.g. preferably they exceed) those normally encountered in the predetermined growing area. This information for a given soil sample can be obtained by conventional soil analysis. In all instances it is essential that each water-soluble inorganic salt which is present in the soil sample in an injurious concentration also is present in the second tissue medium in a similar or greater concentration.

The second culture medium next is visually observed to locate infrequently occurring colonies of cells which are still living. Commonly such living cells will be green in coloration rather than the brown coloration of non-living cells. The cells preferably are present in the second culture medium for at least 30 days, and most preferably for at least 40 days before surviving living cells are identified. These cells may be removed with a probe or by excision in accordance with standard culture techniques.

The living cells which are recovered from the second tissue culture medium next are regenerated (i.e., are elaborated) outside the second tissue culture medium into at least one complete plant via standard biotechnology techniques. Commonly the cells initially are placed on an appropriate growth medium to induce the growth of at least one shoot and this shoot subsequently is transferred to another medium where roots are formed at the base of the shoot. This grows into a mature plant.

It is noted that the resulting plant successfully can be grown in either a non-saline soil or in a soil containing the same plurality of deleterious salts present in the second tissue culture medium in a similar concentration. The genotype of the resulting plant with respect to enhanced salt tolerance can be investigated by self-pollinating the resulting plant through a series of successive generations. If the resulting plant possesses an atypical functioning single gene which is homozygous dominant (i.e., AA) for increased tolerance to the totality of salts present in the second tissue culture medium, then all progeny through successive generations will manifest the desired phenotype. Alternatively, if the resulting plant possesses an atypical functioning single gene which is heterozygous dominant (i.e., Aa) for increased tolerance to the totality of salts present in the second tissue culture medium, then three-quarters of the first generation progeny (i.e., AA, Aa, Aa, aa) will exhibit the increased tolerance to the totality of the salts present in the second tissue culture medium. The plants which do not exhibit the desired phenotype are of no value (i.e. the aa plants are discarded), and the remaining plants (i.e., the AA, Aa, and Aa plants) are again self-pollinated. Since only the plants which are homozygous dominant (i.e., AA) for the desired trait yield progeny which do not segregate with respect to this trait, these can be readily selected and preserved. Seed from such plants can be planted, and multiplied through self-pollination to form a seed product consisting of a substantially homogeneous assemblage of seeds which upon germination yield plants which exhibit the desired enhanced tolerance to the plurality of deleterious salts. Also, this seed can be grown to form a substantially uniform stand of at least one acre of plants which possess the desired enhanced tolerance to the plurality of deleterious salts. Accordingly, crops can be harvested in increased yields from populations of plants of the present invention which are grown in soil containing a normally deleterious concentration of a plurality of inorganic salts.

The following example is set forth as a preferred embodiment of the claimed invention. It should be understood, however, that the invention is not limited to the specific details set forth in the example.

EXAMPLE

It was observed that flax plants (Linum unsitatissimum) of the McGregor variety grew poorly in a saline soil of Saskatchewan, Canada, which contained a deleterious concentration of a plurality of water-soluble inorganic salts. Such soil contained a plurality of water-soluble sulfate salts in a relatively high concentration and exhibited an electrical conductivity of approximately 24 mS/cm. when tested with a Wenner Array four probe resistivity meter. The concentrations of the major cations and anions present in the soil were as indicated hereafter. The McGregor variety can be relied upon to perform well in non-saline soils and is widely grown in such soils.

Flax seedlings of the McGregor variety were germinated under sterile conditions in the laboratory. When the seedlings were approximately 2 to 3 days old, plant tissue from the hypocotyl measuring approximately 1 to 3 mm.$^3$ was obtained by cutting. This plant tissue comprised at least 7 million cells and was plated upon an agar-solidified (0.8% w/v agar in liquid) standard Murashige and Skoog tissue culture medium to which were added 2 mg./l. of 2,4-D hormone and 2.5% w/v of sucrose. A deleterious concentration of inorganic salts was absent in this culture medium. The agar bearing the tissue was supported by petri plates which were sealed with a vapor impervious clear plastic film. After 18 days a similar fresh Murashige and Skoog tissue culture medium was substituted for the medium initially provided to which was added 1 mg./l. of kinetin hormone. After another week living explants or calli in which disorganized call growth was taking place were visible on the culture medium. Because of their relatively large size these were then cut into 2 or 3 portions and were again plated upon a similar fresh Murashige and Skoog tissue culture medium to which was added 1 mg./l. of kinetin hormone. After 20 more days healthy light green calli were removed from the tissue culture medium. While cells of the McGregor variety were present on the tissue culture medium over this 45 day period, genetic somaclonal variation took place, as indicated hereafter.

The living disorganized tissue so obtained in the form of 52 calli was next plated upon a different agar-solidified (0.8% w/v agar in liquid) Murashige and Skoog tissue culture medium which was lacking in a hormone component and which contained the same plurality of deleterious water-soluble salts which were found in the Saskatchewan soil where the McGregor variety of flax was known to grow poorly. A comparison of the concentrations of the major cations and anions present in the soil and in this tissue culture medium is presented below:

| Ion Identification | Concentration in Saskatchewan Soil Sample (parts per million) | Concentration in Tissue Culture Medium (parts per million) |
|---|---|---|
| $Na^+$ | 2,510 | 2,502 |
| $Ca^{++}$ | 450 | 450 |
| $Mg^{++}$ | 3,350 | 3,350 |
| $K^+$ | 130 | 734 |
| $Cl^-$ | 220 | 210 |
| $SO_4^=$ | 18,500 | 19,560 |

The sources for the additional inorganic salts added the basal Murashige and Skoog culture medium were $Na_2SO_4$, $CaSO_4$, and $MgSO_4.7H_2O$. The electrical conductivity of this tissue culture medium containing the deleterious concentration of a plurality of water-soluble inorganic salts was approximately 24 mS/cm. when tested with a conventional laboratory conductivity meter.

After 32 days in the tissue culture medium comprising the deleterious concentration of a plurality of water-soluble salts, the calli were visually inspected to locate infrequently occurring colonies of cells which had survived. Nine pockets of green living cells were next aseptically transferred to another Murashige and Skoog tissue culture medium which was supplemented with 2 mg./l. indolebutyric acid hormone and 1 mg./l of kinetin hormone, and with 3% w/v of sucrose. It was observed that shoots arose from the green living cells in this medium. After two weeks in this growth medium the shoots were partially inserted in Gamborg's B5 medium [See, Can. J. Gen. Cytol. 19, 177–186 (1977)]to promote rooting. When rooting occurred, the plantlets were washed to remove any adhering agar and were transferred to sterile vermiculite in a greenhouse under high humidity conditions.

A single plant when subjected to self-pollination through three generations was proven initially to possess an atypical functioning single gene which was heterozygous dominant for increased tolerance to the totality of salts present in the normally injurious concentration in the second culture medium. Such self-pollination followed by selection for increased tolerance ultimately yielded plants which possessed an atypical functioning single gene which was homozygous dominant for the increased tolerance to the totality of the salts present in the normally injurious concentration in the second culture medium.

Plants obtained by the process of the present invention as heretofore described, were tested in a greenhouse and the results compared with the performance of the usual McGregor variety under various sets of growing conditions. More specifically, these plants were grown in a standard non-saline soil having an electrical conductivity of approximately 1 mS/cm., and in saline soils having electrical conductivities of 8 and 16 mS/cm. which were attributable to the same proportions of normally deleterious water-soluble inorganic salts present in the second culture medium but in lesser overall concentrations. The electrical conductivities were determined using a conventional laboratory conductivity meter. Tolerance to the plurality of inorganic salts was primarily determined by recording the average height of the plants over a specified period of time under constant growing conditions.

When second generation plants of the present invention were measured during the summer for height after 47 days and compared with the usual McGregor variety growing under identical conditions in a greenhouse, the following results were observed:

| Soil Condition (mS/cm.) | Average Height of Plants of McGregor Variety | Average Height of Plants of Present Invention |
|---|---|---|
| E.C. 1 (non-saline) | 29.5 cm. | 31.4 cm. |
| E.C. 8 (highly saline) | 21.7 cm. | 29.5 cm. |

Accordingly, it was observed that second generation flax plants of the present invention grew about as well under highly saline conditions attributable to a plurality of deleterious inorganic salts as plants of the McGregor variety when grown under substantially non-saline conditions.

When third generation plants of the present invention were measured during the summer for height after 48 days and compared with the usual McGregor variety growing under identical conditions in a greenhouse, the following results were observed:

| Soil Condition (mS/cm.) | Average Height of Plants of McGregor Variety | Average Height of Plants of Present Invention |
|---|---|---|
| E.C. 1 (non-saline) | 24.4 cm. with no flowering | taller than 32 cm. with more than 12% flowering |
| E.C. 8 (highly saline) | 18.7 cm. with no flowering | 32 cm. with 12% flowering |
| E.C. 16 (very highly saline) | 12.7 cm with no flowering | 23.5 cm. with 4% flowering |

Accordingly, it was observed that third generation flax plants of the present invention grew about as well under very highly saline conditions attributable to a plurality of deleterious inorganic salts as the McGregor variety when grown under substantially non-saline conditions.

Although the invention has been described with a preferred embodiment, it is to be understood that variations and modifications may be employed without departing from the concept of the invention as defined in the following claims.

I claim:

1. A process for providing plants of a non-halophytic angiosperm crop which is capable of undergoing self-pollination having an enhanced ability to grow successfully in a soil comprising a noramlly deleterious concentration of a plurality of inorganic salts comprising:
   (a) tissue culturing in vitro in a first culture medium a substantial quantity of cells derived from at least one of said plants of said non-halophytic angiosperm crop in the absence of a deleterious concentration of inorganic salts wherein substantial disorganized cell growth takes place which is accompanied by genetic variation,
   (b) tissue culturing in vitro cells from said first culture medium in a second culture medium which is substantially lacking in a hormone component and comprises a plurality of inorganic salts which are provided in a concentration which is normally injurious to cells of said crop wherein a substantial quantity of said cells are killed and at least one cell survives and multiplies which has undergone genetic variation wherein an atypical functioning single gene is present which is dominant for increased tolerance to the totality of salts present in said normally injurious concentration in said second culture medium,
   (c) recovering from said second culture medium living cells which possess said genetic variation, and
   (d) regenerating at least one complete plant from said cells which were receovered in step (c).

2. A process for providing plants of a non-halophytic angiosperm crop having an enhanced ability to grow successfully in a soil comprising a normally deleterious concentration of a plurality of inorganic salts according to claim 1 wherein said non-halophytic angiosperm crop which is capable of undergoing self-pollination selected for tissue culturing in step (a) exhibits substantially reduced growth when growth is attempted in a soil containing a plurality of inorganic salts having an electrical conductivity of 8 mS/cm.

3. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said cells introduced into said first culture medium are derived from at least one seedling plant.

4. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein at least approximately 5 million cells are initially provided in step (a).

5. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said crop is selected from the group consisting of grain crops, forage crops, seed propagated fruits, and industrial species.

6. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said crop is *Linum usitatissimum*.

7. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said disorganized cell growth occurs in a callus.

8. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said disorganized cell growth occurs in a suspension.

9. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein in step (b) the at least one cell which has undergone genetic variation wherein an atypical functioning single gene is present is homozygous dominant for increased tolerance to the totality of salts present in said normally injurious concentration in said second culture medium.

10. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein in step (b) the at least one cell which has undergone genetic variation wherein an atypical functioning single gene is present is heterozygous dominant for increased tolerance to the totality of salts present in said normally injurious concentration in said second culture medium.

11. A process for providing plants of a non-halophytic angiosperm crop which is capable of undergoing self-pollination having an enhanced ability to grow successfully in a soil comprising a normally deleterious concentration of a plurality of inorganic salts according to claim 1 wherein said plurality of inorganic salts provided in said second culture medium each correspond qualitatively to the deleterious salts normally encountered in a predetermined growing area where plant growth of said crop normally is impaired and the respective quantities of said plurality of inorganic salts at least approximate those normally encountered in said predetermined growing area.

12. A process for providing plants of a non-halophytic angiosperm crop which is capable of undergoing self-pollination having an enhanced ability to grow successfully in a soil comprising a normally deleterious concentration of a plurality of inorganic salts comprising:
(a) tissue culturing in vitro in a first culture medium a substantial quantity of cells derived from at least one of said plants of said non-halophytic angiosperm crop in the absence of a deleterious concentration of inorganic salts wherein substantial disorganized cell growth takes Place which is accompanied by genetic variation,
(b) tissue culturing in vitro cells from said first culture medium in a second culture medium which is substantially lacking in a hormone component and comprises a plurality of inorganic salts which are provided in a concentration which is noramlly injurious to cells of said crop wherein a substantial quantity of said cells are killed and at least one cell survives and multiplies which has undergone genetic variation wherein an atypical functioning single gene is present which is heterozygous dominant for increased tolerance to the totality of salts present in said normally injurious concentration in said second culture medium,
(c) recovering from said second culture medium living cells which possess said genetic variation,
(d) regenerating at least one complete first generation plant from said cells which were recovered in step (c),
(e) self-pollinating at least one functioning first generation plant from step (d) to form seed thereon,
(f) growing said seed from step (e) to form second generation plants,
(g) selecting those second generation plants from step (f) which exhibit increased tolerance to the totality of salts present in said normally injurious concentration in said second culture medium and allowing seed to form thereon following self-pollination,
(h) growing said seed from step (g) to form third generation plants, and
(i) selecting those third generation plants which possess a single gene which is homozygous dominant for increased tolerance to the totality of salts present in said normally injurious concentration in said second culture medium.

13. A process for providing plants of a non-halophytic angiosperm crop which ia capable of undergoinS self-pollination having an enhanced ability to grow successfully in a soil comprising a normally deleterious concentration of a plurality of inorganic salts according to claim 12 wherein said non-halophytic angiosperm crop selected for tissue culturing in step (a) exhibits substantially reduced growth when growth is attempted in a soil containing a plurality of inorganic salts having an electrical conductivity of 8 mS/cm.

14. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said cells introduced into said first culture medium are derived from at least one seedling plant.

15. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein at least approximately 5 million cells are initially provided in step (a).

16. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said crop is selected from the group consisting of grain crops, forage crops, seed propagated fruits, and industrial species.

17. A process for providing plants of a non-halophytic angiosperm crop having an enhanced ability to grow successfully in a soil comprising a normally deleterious concentration of a plurality of inorganic salts according to claim 12 wherein said crop is *Linum usitatissimum*.

18. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said disorganized cell growth occurs in a callus.

19. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said disorganized cell growth occurs in a suspension.

20. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein cells are provided in said first culture medium for at least 30 days and in said second culture medium for at least 30 days.

21. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said genetic variation occurs via somaclonal variation in said first culture medium in the substantial absence of a mutagen.

22. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said genetic variation which occurs in said first culture medium is at least in part induced by a mutagen.

23. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said first culture medium contains at least one hormone which is capable of promoting said disorganized cell growth and said second culture medium is substantially lacking in a hormone component.

24. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein the cations of said plurality of inorganic salts provided in said second culture medium in a concentration which is normally injurious to cells of said crop are selected primarily from the group consisting of alkali metals, alkaline earth metals, and mixtures thereof.

25. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said plurality of inorganic salts provided in said second culture medium in a concentration which is normally injurious to cells of said crop comprise at least two sulfate salts.

26. A process for providing plants of a non-halophytic angiosperm crop which is capable of undergoing self-pollination having an enhanced ability to grow successfully in a soil comprising a normally deleterious concentration of a plurality of inorganic salts according to claim 12 wherein said plurality of inorganic salts provided in said second culture medium each correspond qualitatively to the deleterious salts normally encountered in a predetermined growing area where plant growth of said crop normally is impaired and the respective quantities of said plurality of inorganic salts at least approximate those normally encountered in said predetermined growing area.

27. A process for providing plants of *Linum usitatissimum* having an enhanced ability to grow successfully in a soil comprising a normally deleterious concentration of a plurality of inorganic salts comprising:
(a) tissue culturing in vitro in a first culture medium in the presence of at least one hormone at least approximately 5 million cells derived from at least one of said *Linum usitatissimum* plants in the absence of a deleterious concentration of inorganic salts wherein substantial disorganized cell growth takes place which is accompanied by genetic somaclonal variation,
(b) tissue culturing in vitro cells from said first culture medium in a second culture medium which is substantially lacking in a hormone component, and a mutagen and which comprises a plurality of inorganic salts which are provided in a concentration which is normally injurious to cells of said plants wherein a substantial quantity of said cells are killed and at least one cell survives and multiplies which has undergone genetic somaclonal variation wherein an atypical functioning single gene is present which is heterozygous dominant for increased tolerance to the totality of salts present in said normally injurious concentration in said second culture medium,
(c) recovering from said second culture medium living cells which possess said genetic somaclonal variation,
(d) regenerating at least one complete first generation plant from said cells which were recovered in step (c),
(e) self-pollinating said at least one functioning first generation plant from step (d) to form seed thereon,
(f) growing said seed from step (e) to form second generation plants,
(g) selecting those second generation plants from step (f) which exhibit increased tolerance to the totality of salts present in said normally injurious concentration in said second culture medium and allowing seed to form thereon following self-pollination,
(h) growing said seed from step (g) to form third generation plants, and
(i) selecting those third generation plants which possess a single gene which is homozygous dominant for increased tolerance to the totality of salts present in said normally injurious concentration in said second culture medium.

28. A process for providing plants of *Linum usitatissimum* having an enhanced ability to grow successfully in a soil comprising a normally deleterious concentration of a plurality of inorganic salts according to claim 27 wherein said non-halophytic angiosperm crop selected for tissue culturing in step (a) exhibits substantially reduced growth when growth is attempted in a soil containing a plurality of inorganic salts having an electrical conductivity of 8 mS/cm.

29. A process for providing plants of *Linum usitatissimum* having an enhanced ability to grow successfully in a soil comprising a normally deleterious concentration of a plurality of inorganic according to claim 27 wherein said cells introduced into said first culture medium are derived from the McGregor variety.

30. A process for providing plants of Linum usitatissimum having an enhanced ability to grow successfully in a soil comprising a normally deleterious concentration of a plurality of inorganic salts according to claim 27 wherein said cells introduced into said first culture medium are derived from at least one seedling plant.

31. A process for providing plants of *Linum usitatissimum* having an enhanced ability to grow successfully in a soil comprising a normally deleterious concentration of a plurality of inorganic salts according to claim 27 wherein said cells introduced into said first culture medium are derived from the hypocotyl of at least one of said plants obtained soon following germination.

32. A process for providing plants of *Linum usitatissimum* having an enhanced ability to grow successfully in a soil comprising a normally deleterious concentration of a plurality of inorganic salts according to claim 27 wherein said disorganized cell growth occurs in a callus.

33. A process for providing plants of *Linum usitatissimum* having an enhanced ability to grow successfully in a soil comprising a normally deleterious concentration of a plurality of inorganic salts according to claim 27 wherein said disorganized cell growth occurs in a callus in a Murashige and Skoog medium.

34. A process for providing plants of *Linum usitatissimum* having an enhanced ability to grow successfully in a soil comprising a normally deleterious concentration of a plurality of inorganic salts according to claim 27 wherein said disorganized cell growth occurs in a suspension.

35. A process for providing plants of *Linum usitatissimum* having an enhanced ability to grow successfully in a soil comprising a normally deleterious concentration of a plurality of inorganic salts according to claim 27 wherein cells are provided in said first culture medium for at least 30 days and in said second culture medium for at least 30 days.

36. A process for providing plants of *Linum usitatissimum* having an enhanced ability to grow successfully in a soil comprising a normally deleterious concentration of a plurality of inorganic salts according to claim 27 wherein the cations of said plurality of inorganic salts provided in said second culture medium in a concentration which is normally injurious to cells of said crop are selected primarily from the group consisting of alkali metals, alkaline earth metals, and mixtures thereof.

37. A process for providing plants of *Linum usitatissimum* having an enhanced ability to grow successfully in a soil comprising a normally deleterious concentration of a plurality of inorganic salts according to claim 27 wherein said plurality of inorganic salts provided in said second culture medium in a concentration which is normally injurious to cells of said crop comprise at least two sulfate salts.

38. A process for providing plants of *Linum usitatissimum* crop having an enhanced ability to grow successfully in a soil comprising a normally deleterious concentration of a plurality of inorganic salts according to claim 27 wherein said plurality of inorganic salts provided in said second culture medium each correspond qualitatively to the deleterious salts normally encountered in a predetermined growing area where plant growth of said crop normally is impaired and the respective quantities of said plurality of inorganic salts at least approximate those normally encountered in said predetermined growing area.

39. A *Linum usitatissimum* seed product consisting of a substantially homogeneous assemblage of seeds which upon germination yield flax plants which exhibit an enchanced ability to grow successfully in soil comprising a normally deleterious concentration of a plurality of inorganic salts with said plants being capable of growth in a soil containing a plurality of inorganic salts having an electrical conductivity of 8 mS/cm. to yield a commercial product on a successful basis, and wherein said enhancement in salt tolerance to the totality of said inorganic salts is attributable to the presence of a single homozygous dominant gene for such characteristic.

40. A *Linum usitatissimum* seed product according to claim 39 which was derived from cells of the McGregor variety employing tissue culture in vitro and genetic modification.

41. A *Linum usitatissimum* seed product according to claim 39 which was derived from cells of the McGregor variety via tissue culture in vitro accompanied by somaclonal variation in the substnatial absence of a mutagen.

42. A substantially uniform stand of plants of *Linum usitatissimum* which exhibit an enhanced ability to grow successfully in soil comprising a normally deleterious concentration of a plurality of inorganic salts with said plants being capable of growth in soil containing a plurality of inorganic salts having an electrical conductivity of 8 mS/cm. to yield a commercial product on a successful basis, and wherein said enhancement in salt tolerance to the totality of said inorganic salts is attributable to the presence of a single homozygous dominant gene for such characteristic.

43. Plants of *Linium usitatissimum* according to claim 42 which were derived from cells of the McGregor variety employing tissue culture in vitro and genetic modification.

44. Plants of *Linum usitatissimum* according to claim 42 which were derived from cells of the McGregor variety via tissue culture in vitro accompanied by somaclonal variation in the substantial absence of a mutagen.

45. Plants of *Linum usitatissimum* according to claim 42 which are present in a substantially uniform stand of at least one acre.

* * * * *